US011350609B1

(12) United States Patent
Goldenberg

(10) Patent No.: US 11,350,609 B1
(45) Date of Patent: Jun. 7, 2022

(54) SCORPION VENOM EXTRACTION UNIT

(71) Applicant: Joshua Goldenberg, Waban, MA (US)

(72) Inventor: Joshua Goldenberg, Waban, MA (US)

( * ) Notice: Subject to any disclaimer, the term of this patent is extended or adjusted under 35 U.S.C. 154(b) by 0 days.

(21) Appl. No.: 17/208,265

(22) Filed: Mar. 22, 2021

(51) Int. Cl.
*A01K 29/00* (2006.01)
*A01K 67/033* (2006.01)

(52) U.S. Cl.
CPC ............ *A01K 29/00* (2013.01); *A01K 67/033* (2013.01)

(58) Field of Classification Search
CPC .............................. A01K 29/00; A01K 67/033
See application file for complete search history.

(56) References Cited

FOREIGN PATENT DOCUMENTS

| CA | 3065184 A1 | * | 4/2020 | |
|---|---|---|---|---|
| CN | 2031605 U | * | 2/1989 | |
| CN | 2049116 U | * | 12/1989 | |
| CN | 2076826 U | * | 11/1990 | |
| CN | 2333183 Y | * | 8/1999 | |
| CN | 1238907 A | * | 12/1999 | |
| CN | 2529511 Y | * | 1/2003 | |
| CN | 101336622 A | * | 1/2009 | |
| CN | 203243839 U | * | 10/2013 | |
| CN | 102308775 B | * | 11/2013 | |
| CN | 103767181 A | * | 5/2014 | |
| CN | 103798192 A | * | 5/2014 | |
| CN | 203675883 U | * | 7/2014 | |
| CN | 203952166 U | * | 11/2014 | |
| CN | 204350854 U | * | 5/2015 | |
| CN | 108552118 A | * | 9/2018 | ........... A01K 67/033 |

OTHER PUBLICATIONS

Michelen, A., "A New Method to Extract Scorpion Venom", <URL: https://insights.globalspec.com/article/5742/a-new-method-to-extract-scorpion-venom>, Engineering 360, GlobalSpec, Jul. 5, 2017,accessed Dec. 28, 2021 (2 pages).
Scott, G. "Scientists Have Invented A Scorpion-Milking Robot", <URL: https://www.inverse.com/article/33679-scientists-have-invented-a-scorpion-milking-robot>, Inverse, Jul. 2, 2017, accessed Dec. 28, 2021 (2 pages).
Shah, S., "A robot that milks scorpions could aid cancer research", <URL: https://www.engadget.com/2017-07-04-a-robot-that-milks-scorpions-could-aid-cancer-research.html>, Endgadget, dated Jul. 5, 2017, accessed Dec. 28, 2021 (3 pages).

* cited by examiner

*Primary Examiner* — Magdalena Topolski
*Assistant Examiner* — Alanna K Peterson
(74) *Attorney, Agent, or Firm* — Wilmer Cutler Pickering Hale and Dorr LLP

(57) ABSTRACT

A portable, handheld, unit for extracting scorpion venom is disclosed. The unit includes body and tail restraints for restraining a scorpion such that the scorpion is held safely and humanely. When restrained, the scorpion's tail extends beyond an end of the unit and over a retractable venom receptacle. The unit also includes a chamber for holding a reservoir of cleaning fluid and a mechanical switch for expelling fluid from the reservoir onto the scorpion's stinger. The unit also includes a fan for drying the cleaned scorpion's stinger. The unit also includes a wire for delivering an electrical current to the scorpion's tail to cause the scorpion to express its venom into the venom receptacle.

7 Claims, 5 Drawing Sheets

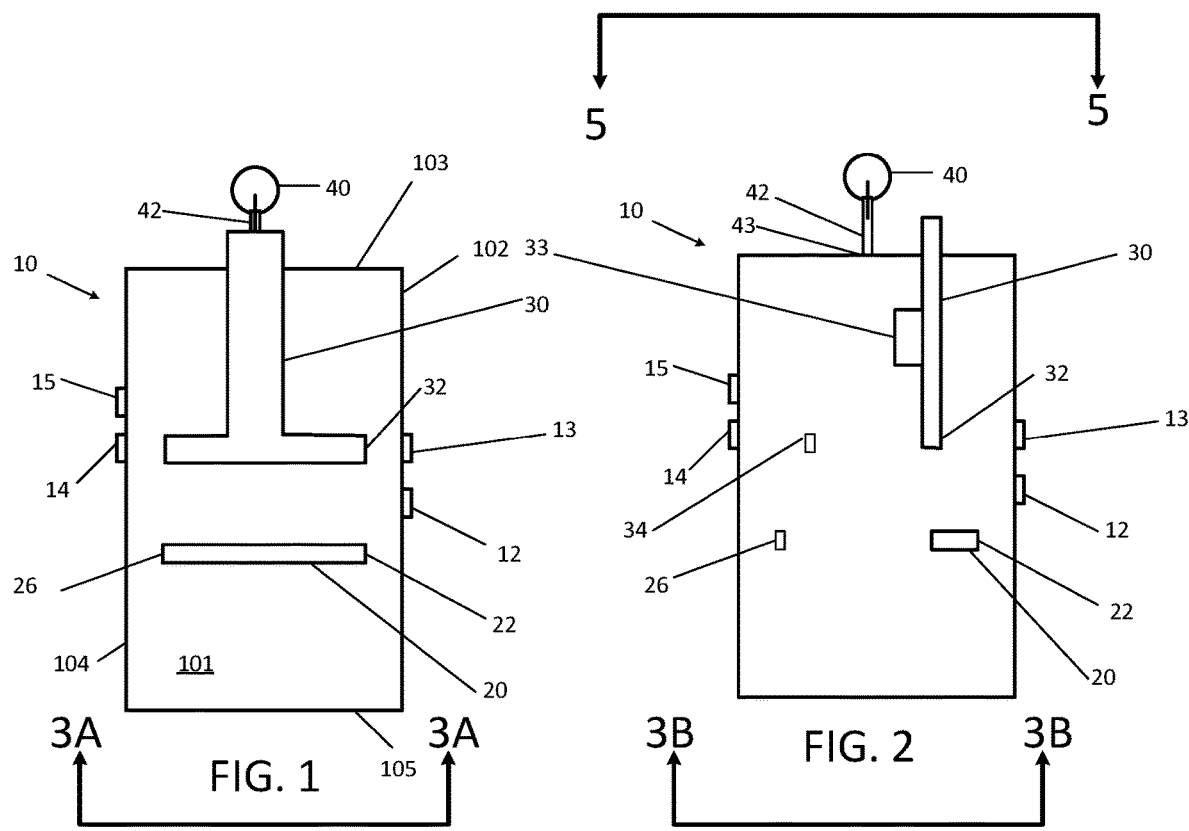

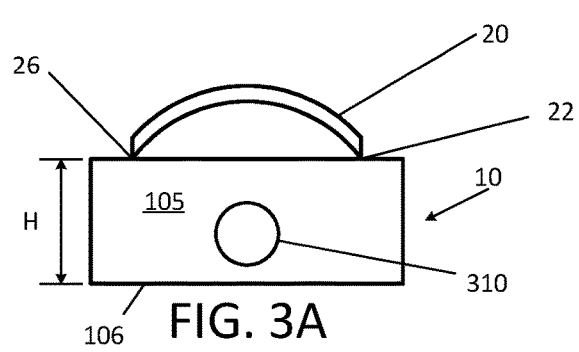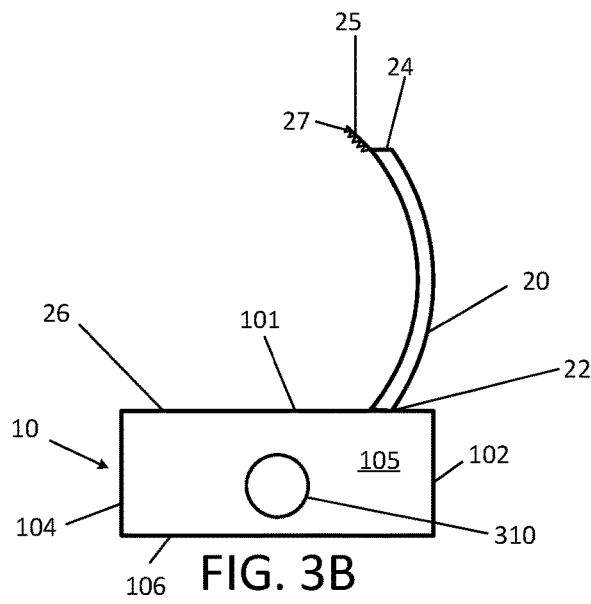

SCORPION VENOM EXTRACTION UNIT

BACKGROUND

This disclosure relates to extraction of scorpion venom in a manner that is both safe for the human operator and humane for the scorpion.

Scorpion venom is a valuable commodity, e.g., in the field of pharmaceutical research. The venom of the deathstalker scorpion is particularly valuable. However, extracting scorpion venom, particularly that of the deathstalker scorpion, can be both difficult and dangerous.

BRIEF SUMMARY OF THE INVENTION

The invention provides safe and humane techniques extracting scorpion venom. In particular, the invention provides safe and humane techniques for extracting deathstalker scorpion venom.

Preferred embodiments include a portable handheld unit. A human operator can use tongs, or some other safety device, to place a scorpion, such as a deathstalker scorpion, onto the unit. Using thumb and fingers of one hand, the operator can manipulate restraining arms that safely and humanely hold the scorpion onto the unit. Once the scorpion has been restrained, the operator can manipulate buttons and switches to (a) clean the scorpion's stinger and portions of the scorpion's tail near the stinger, (b) dry the stinger, (c) move a venom receptacle beneath the stinger, and (d) apply an electric current to the tail near the stinger causing the scorpion to express its venom such that the venom is collected in the receptacle.

After a scorpion's venom has been collected in the receptacle, the operator can, again using thumb and fingers, release the restraining arms and use tongs to return the scorpion to its living area, e.g., a terrarium or the wild. The venom in the receptacle can then be transferred to a larger venom holding receptacle and ultimately sold, e.g., to pharmaceutical researchers.

BRIEF DESCRIPTION OF THE DRAWINGS

The foregoing and other objects of this invention, the various features thereof, as well as the invention itself, may be more fully understood from the following description, when read together with the accompanying drawings in which:

FIG. 1 shows a top view of a scorpion venom extraction unit constructed in accordance with the invention with restraining arms in a closed, or restraining, position.

FIG. 2 shows a top view of the unit shown in FIG. 1 with restraining arms in an open, or released, position.

FIG. 3A shows a front view of the unit shown in FIG. 1 from the perspective illustrated by arrow 3A-3A in FIG. 1.

FIG. 3B shows a front view of the unit shown in FIG. 2 from the perspective illustrated by arrow 3B-3B in FIG. 2.

Like numbered elements in each FIGURE represent the same or similar elements.

DETAILED DESCRIPTION OF THE INVENTION

Figure 4A:
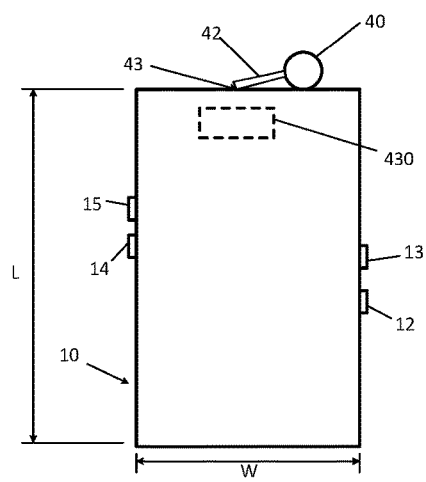
FIG. 4A shows a top view of the unit shown in FIG. 1 with some components removed for ease of exposition.

FIGS. 1-5 show various views of a portable handheld unit 10 for extracting scorpion venom. In the illustrated embodiment, unit 10 is a cuboid shape having six generally rectangular surfaces 101-106 (e.g., with surfaces 101-105 shown in FIG. 1 and surface 106 shown in FIG. 3A). For ease of exposition, surface 101 will be referred to herein as a top surface, surface 102 will be referred to herein as a right surface, surface 103 will be referred to herein as a back surface, surface 104 will be referred to herein as a left surface, surface 105 will be referred to herein as a front surface and surface 106 (shown in FIG. 3A) will be referred to herein as a bottom surface. Those of ordinary skill will appreciate that the references top, bottom, left, right, front and back are merely relative and not inherent properties of unit 10. Preferably unit 10 is sized to fit comfortably within a human hand with bottom surface 106 (shown in FIG. 3A) resting in the palm of the hand. When unit 10 is held by a right hand of a human operator with the bottom surface 106 resting in the palm of the hand, and the unit being held upright as it would during a venom extraction process, then top surface 101 (shown in FIG. 1) would be above bottom surface 106, and left surface 104 would be to the left of right surface 102. Those of ordinary skill will appreciate that the unit 10 can be held and operated in different ways and further that unit 10 can be formed in other shapes as well, e.g., ovoid shapes. References herein to the location of various surfaces are made merely to advance explanation and not to limit the invention.

FIGS. 1 and 2 show top views of a unit 10. Unit 10 includes an electrical switch 12, a mechanical switch 13, an electrical switch 14, and a mechanical switch 15. Preferably unit 10 is sized such that when bottom surface 106 (shown in FIG. 3B) rests in the palm of a human operator's right hand, switches 12 and 13 can be comfortably manipulated by the operator's right thumb and switches 14 and 15 can be comfortably manipulated by the fingers of the operator's right hand.

Unit 10 includes a body restraint 20 and a tail restraint 30. As with switches 12 and 13, when unit 10 is resting in the palm of the operator's right hand, the restraints 20 and 30 can be manipulated by the operator's right thumb. Unit 10 also includes a venom receptacle 40 and a venom receptacle holder arm 42 (shown, e.g., in FIG. 2).

FIG. 1 shows the body restraint 20 and tail restraint 30 in a closed, or restraining, position, whereas FIG. 2 shows body and tail restraints 20 and 30 in an open, or non-restraining, position. FIGS. 3A and 3B, discussed further below, show body restraint 20 in closed and open positions, respectively.

Body restraint 20 is movably (e.g., rotatably) coupled to unit 10 by coupling 22, which can be for example a hinge. Similarly, tail restraint 30 is movably (e.g., rotatably) coupled to unit 10 by coupling 32, which can be for example a hinge.

Figure 12:
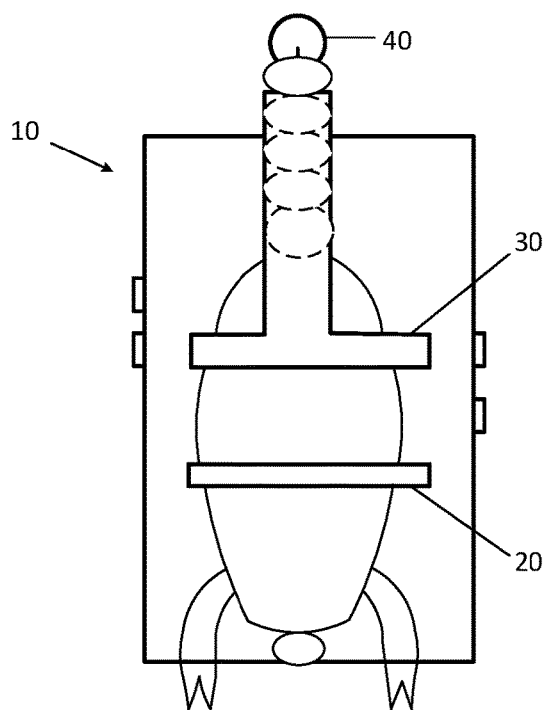
FIG. 12 shows a top view of the unit shown in FIG. 1 with a scorpion restrained on the unit.

In operation, an operator would begin a venom extraction procedure by placing the restraints 20 and 30 in the open position as shown in FIG. 2. The operator would then use tongs or other safety equipment to place a scorpion on unit 10 such that the scorpion's back is in contact with, and supported by, top surface 101 as shown generally in FIG. 12. The operator would then move body restraint 20 from the open position (as shown in FIG. 2) to the closed position (as shown in FIG. 1). For example, in embodiments with a rotatable coupling 22 the operator pushes body restraint 20 such that the restraint 20 rotates about coupling 22 and thereby moves from the open position (shown in FIG. 2) to the closed position (shown in FIG. 1).

When the body restraint 20 is in the closed position, the free-end 24 (shown, e.g., in FIG. 3B) of restraint 20 (i.e., the end of restraint 20 that is not attached to coupling 22) is fixed to unit 10 by clasp 26. Engagement between free-end 24 and clasp 26 can be implemented using all manner of clasps. One preferred choice for free-end 24 and clasp 26 is the well-known type of clasp used in handcuffs, e.g., a clasp that allows free-end 24 to extend further into unit 20 in response to pressure on restraint 20, such that the clasp emits audible "clicks" as free-end 24 extends further into unit 10. Use of such a clasp allows the unit 10 to accommodate scorpions of various size. That is, by pushing free-end 24 further, or less far, into unit 10 the body restraint 20 can snugly hold scorpions of different sizes, securely and humanely, to unit 10. Regardless of the particular type of clasp used, activating mechanical switch 13, e.g., by depressing it, releases clasp 26 allowing body restraint 20 to be moved from the closed position (shown in FIG. 1) to the open position (shown in FIG. 2).

Returning to the operation of unit 10, once the operator has restrained the body of a scorpion by moving restraint 20 from the open position (shown in FIG. 2) to the closed position (shown in FIG. 1) such that free-end 24 engages with clasp 26 and such that the body restraint 20 snugly holds the body of the scorpion to the top surface 101, the scorpion's body will have been restrained. The operator would then move the tail restraint 30 from the open position (shown in FIG. 2) to the closed position (shown in FIG. 1) so as to restrain the scorpion's tail (as shown generally in FIG. 12).

In one embodiment, the operator would (a) hold unit 10 in the operator's right hand, (b) use tongs to apply the scorpion to unit 10 and to hold the scorpion in place while the operator moves body restraint 20 from the open position (shown in FIG. 2) to the closed position (shown in FIG. 1), thus restraining the body of the scorpion. At this point, the operator could release the tongs. Alternatively, the operator could use the tongs to hold the scorpion's tail in place while the operator moves the tail restraint from the open position (shown in FIG. 2) to the closed position (shown in FIG. 1). Once the tail restraint is in the closed position (shown in FIG. 1) the scorpion will have been fully restrained and the operator can discard the tongs.

When tail restraint 30 is moved to the closed position, the tail restraint 30 engages with a clasp 34 (shown in FIG. 2) to hold the restraint 30 in the closed position. Whereas the size of adult deathstalker scorpion bodies can vary, there is much less variation in the size of their tails. Accordingly, clasp 34 can be simpler and less adjustable than clasp 26. Although clasp 34 could be implemented using the same type of clasp described above for the body restraint clasp 26, tail restraint clasp 34 can alternately have only a single (non-adjustable) closed position. As an example, clasp 34 can be implemented using the type of clasp commonly used for securing a battery cover plate in a television remote control. As with body restraint clasp 26, the tail restraint clasp 34 can be released by activating mechanical switch 13. Alternately, tail restraint 30 can be released from clasp 34 by manipulating the clasp or restraint directly, e.g., as is done with battery cover plates in television remote controls. As yet another alternative, unit 10 can contain an additional switch for releasing tail restraint 30 from clasp 34.

Once the operator has restrained the scorpion, by moving restraints 20, 30 to the closed position, the operator can continue the venom extraction process by performing these steps, each of which is described further below: (a) cleaning the scorpion's stinger by spraying a cleaning solution, such as saline, onto the stinger in response to manipulation of mechanical switch 15, (b) drying the scorpion's stinger, e.g., by using a fan controlled by electrical switch 14, (c) moving venom receptacle 40 such that it is disposed beneath the scorpion's stinger, and (d) electrically connecting a power source to the scorpion's tail near the stinger, in response to manipulation of electrical switch 12, which causes the scorpion to express its venom into receptacle 40.

FIG. 3A shows a front view of unit 10 (showing, e.g., front surface 105) from the perspective illustrated by arrow 3A-3A in FIG. 1. Similarly, FIG. 3B shows a front view of unit 10 from the perspective illustrated by arrow 3B-3B in FIG. 2. FIG. 3A shows body restraint 20 in a closed, or restraining, position. FIG. 3B shows body restraint 20 in an open position. As shown in FIG. 3B, body restraint 20 can include a clasp engagement portion 25 at the free-end 24. Clasp engagement portion 25 can optionally include teeth 27 for engaging with clasp 26. In operation, clasp engagement portion 25 would extend into clasp 26 such that the teeth 27 are gripped by clasp 26. The tightness of the grip between body restraint 20 and the scorpion can be adjusted by pushing engagement portion 25 further into clasp thus allowing the snug and humane restraint of scorpions with different body sizes.

FIGS. 3A and 3B also show a channel 310. Channel 310 extends through unit 10 to permit airflow. As explained further below, unit 10 includes a fan which is disposed within channel 310.

FIG. 4A show another top view of unit 10. For ease of exposition, components such as restraining arms 20 and 30 are omitted from FIG. 4A. As shown in FIG. 4A, venom receptacle holder am 42 is movably (e.g., rotatably) coupled to unit 10 by coupling 43, which can be implemented for example as a hinge. FIG. 4A shows an example of a stowed position for venom receptacle 40. Conversely, FIG. 2 shows venom receptacle 40 in a deployed position. If coupling 43 is implemented as a hinge, venom receptacle 40 can be rotated between the stowed position (shown in FIG. 4A) and the deployed position (shown in FIG. 2). Whereas FIGS. 2 and 4A illustrate that venom receptacle arm 42 can swing side-to-side, in other embodiments it can swing up-and-down or in other directions. Those of ordinary skill will also appreciate that coupling 43 can be implemented in various ways and the stowed position of venom receptacle 40 will vary depending on the type of coupling. As another example, coupling 43 can permit holder arm 42 to be retracted within unit 10.

In operation, an operator would move venom receptacle 40 to the stowed position (e.g., as shown in FIG. 4A) when cleaning the scorpion's stinger so as to prevent foreign material, such as sand or saline, from entering the receptacle 40. Conversely, the operator would move venom receptacle 40 to the deployed position (shown in FIG. 2), when stimulating the scorpion so as to cause the scorpion to express its venom.

Figure 4B:
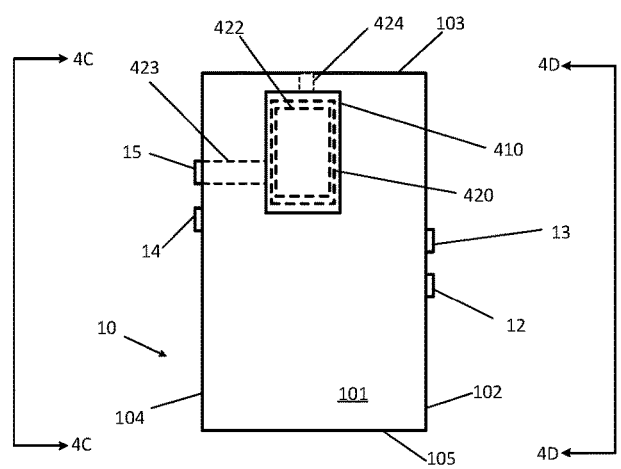
FIG. 4B shows another top view of the unit shown in FIG. 1 with some components removed for ease of exposition.

FIG. 4B shows another top view of unit 10. As with FIG. 4A, components such as restraints 20 and 30 are omitted from FIG. 4B for ease of exposition. As shown in FIG. 4B, unit 10 includes a removable plate 410. Plate 410 can be formed, for example, in the manner of plates commonly used for battery covers in electronic products such as TV remote controls. When removed, plate 410 exposes a chamber 420 within unit 410. Chamber 420 houses a reservoir 422 of cleaning solution such as saline. One preferred choice for reservoir 422 is a flexible plastic bottle. As shown in FIG. 4B, mechanical switch 15 connects to internal rod 423 such that depressing switch 15 pushes rod 423 into bottle 422, thus causing bottle 422 to eject cleaning solution via a channel 424. As explained further below, channel 424 is in fluid communication with chamber 420 and an irrigation port 520 (shown in FIG. 5) and is positioned, along with the irrigation port, such that solution expelled from reservoir 422 is aimed at, and cleans, the scorpion's stinger. In some embodiments, switch 15 and rod 423 are integrally formed as a single solid component.

Figure 4C:
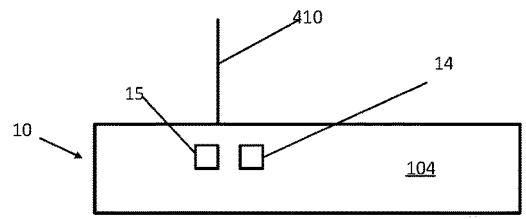
FIG. 4C shows a side view of the unit shown in FIG. 4B from the perspective illustrated by arrow 4C-4C in FIG. 4B.

FIG. 4C shows a side view of the unit 10 (e.g., showing left surface 104) from the perspective illustrated by arrow 4C-4C in FIG. 4B. FIG. 4C shows plate 410 in an open position. Plate 410 can be rotatably coupled to unit 410 such that it can be swiveled between a closed position (as shown in FIG. 4B) or an open position as shown in FIG. 4C. When plate 410 is in the open position (as shown in FIG. 4C) it exposes chamber 420 (shown in FIG. 4B) and allows replacement of reservoir 422. As an alternative to being rotatably coupled, plate 410 may be entirely removable from unit 10 as is commonly done with battery cover plates in commercial electronic devices such as TV remote controls.

Figure 4D:
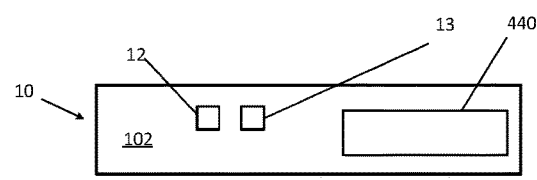
FIG. 4D shows a side view of the unit shown in FIG. 4B from the perspective illustrated by arrow 4D-4D in FIG. 4B.

FIG. 4D shows a side view of the unit 10 (e.g., showing right surface 102) from the perspective illustrated by arrow 4D-4D in FIG. 4B. As shown in FIG. 4D, unit 10 includes a battery cover plate 440. Plate 440 can be removed in conventional fashion to expose a chamber within unit 10 for housing batteries. When installed, the batteries power electric devices within unit 10 such as the fan.

Figure 5:
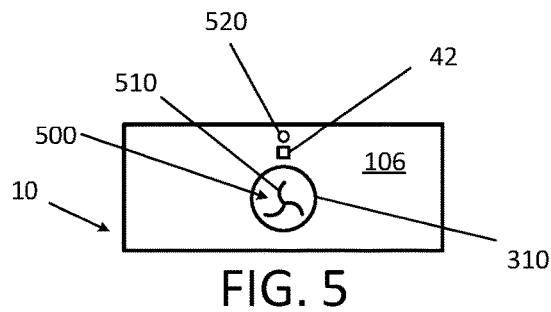
FIG. 5 shows a back view of the unit shown in FIG. 2 from the perspective illustrated by arrow 5-5 in FIG. 2.

FIG. 5 shows a back view of the unit 10 (e.g., showing back surface 106) from the perspective illustrated by arrow 5-5 in FIG. 2. FIG. 5 shows electric fan 500, having fan blades 510, disposed within channel 310. The position of fan 500 within unit 10 is also depicted in FIG. 4A by dashed lines 430. The fan 500 is preferably recessed within unit 10 so that spinning fan blades 510 cannot contact a user's finger. FIG. 5 also shows irrigation port 520 disposed above venom receptacle holder arm 42. Irrigation port 520 is fluidically coupled with chamber 420 (shown in FIG. 4B),
via channel 424, such that depressing mechanical switch 15 causes fluid to be ejected from port 520. Irrigation port 520 is a port from which a cleaning solution, such as saline, is ejected so as to clean the scorpion's stinger. Chamber 420 (shown in FIG. 4A), reservoir 422, channel 424 and irrigation port 520 (shown in FIG. 5) cooperate such that fluid expelled from reservoir 422 and port 520 forms a stream that is aimed at the scorpion's stinger when a scorpion is on unit 10 and retrained by body and tail restraints, 20 and 30 (shown in FIG. 1).

Figure 6:
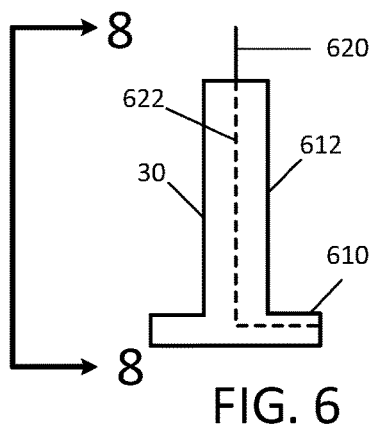
FIG. 6 shows a top view of the main tail restraint shown in FIG. 1.

FIG. 6 shows a top view of tail restraint 30 taken from the same perspective as FIG. 1. That is, FIG. 6 shows a top view of tail restraint 30 when restraint 30 is in the closed position. As shown, when seen from the top, tail restraint 30 is generally T-shaped and includes an arm 610 and a main section 612. FIG. 6 also shows an exposed electrical wire 620 extending beyond the main section 612 of tail restraint 30. Wire 620 is electrically connected to a power source such that switch 12 (shown in FIGS. 1 and 2) can control delivery of electrical power to wire 620. Dashed line 622 shows the path of electrical wire 620 through the body of tail restraint 30. As explained further below, exposed portion of wire 620 is configured to touch the distal end of the scorpion's tail when the scorpion is restrained by both body and tail restraints 20, 30.

Figure 7:
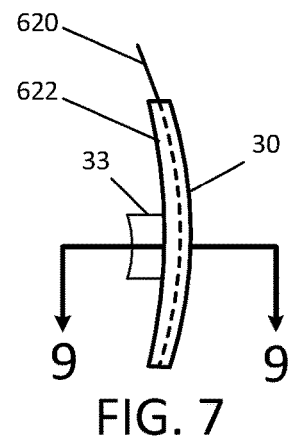
FIG. 7 shows a top view of the main tail restraint shown in FIG. 2.

FIG. 7 shows a top view of tail restraint 30 taken from the same perspective as FIG. 2. That is, FIG. 7 shows a top view of tail restraint 30 when restraint 30 is in the open position. Whereas FIG. 2 shows tail restraint 30 as being straight, FIG. 7 shows it being curved. Those of ordinary skill will appreciate that both straight and curved embodiments of tail restraint 30 may be used. As shown in FIG. 7, tail restraint 30 includes lateral restraints 33 (also shown in FIGS. 9A and 9B as restraints 33a and 33b).

Figure 8:
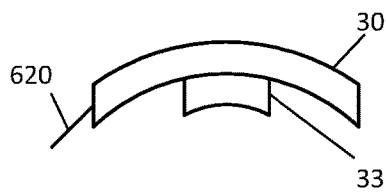
FIG. 8 shows the main tail restraint shown in FIG. 6 from the perspective illustrated by arrow 8-8 in FIG. 6.
Figure 9A:
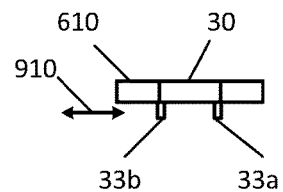
FIG. 9A shows a sectional view of the main tail restraint shown in FIG. 7 from the perspective illustrated by arrow 9-9 in FIG. 7 when the lateral restraints are in one position.
Figure 9B:
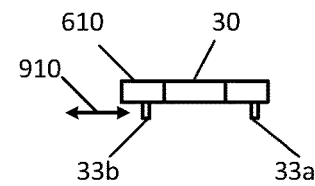
FIG. 9B shows a sectional view of the main tail restraint shown in FIG. 7 from the perspective illustrated by arrow 9-9 in FIG. 7 when the lateral restraints are in a different, wider, position than shown in FIG. 9A.

FIG. 8 shows a side view of tail restraint 30 from the perspective illustrated by arrow 8-8 in FIG. 6. FIGS. 9A and 9B show sectional views of tail restraint 30 from the perspective illustrated by arrow 9-9 in FIG. 7. As shown best in FIGS. 9A and 9B, the lateral restraints 33a and 33b project downward from the main body of the restraint. That is, when tail restraint 30 is in the closed position, the lateral restraints project downwards. When a scorpion is restrained on unit 10, restraints 33a and 33b prevent the scorpion's tail from wriggling, or moving laterally. That is, when tail restraint 30 is in the closed position, lateral restraint 33a (i.e., the restraint 33 closest to left surface 104 as shown in FIG. 1) restricts the ability of the scorpion's tail to move towards left surface 104. Similarly, when tail restraint 30 is in the closed position, lateral restraint 33b (i.e., the restraint 33 closest to right surface 102 as shown in FIG. 1) restricts the ability of the scorpion's tail to move towards right surface 102. The lateral restraints 33a and 33b are also preferably movably coupled to restraint 30 such that they can slide towards or away from each other in the direction indicated by arrow 910.

When tail restraint 30 is initially moved from the open position to the closed position, the lateral restraints 33a and 33b are preferably spaced far apart from one another so that the scorpion's tail easily fits between the restraints 33a and 33b. When the tail restraint 30 is in this position (i.e., the restraint 30 is in the closed position and the restraints 33a and 33b are far apart), the restraint 30 and top surface 101 (shown in FIG. 1) restrict up-down motion of the scorpion's tail, but the restraints 33a and 33b permit some side-to-side motion of the scorpion's tail. Once the tail restraint 30 has been clasped in the closed position, the operator can then slide the lateral restraints 33a and 33b towards one another so as to restrict side-to-side motion of the scorpion's tail.

In operation, when a scorpion is on unit 10 and restrained by body restraint 20 and tail restraint 30, the exposed portion of wire 620 contacts the distal end of the scorpion's tail near to the scorpion's stinger. With the scorpion so restrained, the operator can activate mechanical switch 15 (e.g., as shown in FIG. 4B) so as to clean the scorpion's stinger. That is, activating switch 15 expels fluid, such as saline, from irritation port 520 (shown in FIG. 5) such that the fluid cleans the stinger. For example, activating switch 15 moves rod 423 (shown in FIG. 4B), which in turn squeezes reservoir 422 thus expelling fluid from port 520. Once the scorpion's stinger has been so cleaned, the operator can dry the scorpion's stinger by pressing switch 14 so as to activate fan 500 (shown in FIG. 5). Once the scorpion's stinger has been cleaned and dried, the operator can move the venom collection receptacle 40 from the stowed position (e.g., as shown in FIG. 4A) to the deployed position shown in (FIGS. 1 and 2). The operator can then cause the scorpion to express its venom by activating switch 12, which delivers electrical power via wire 620 (e.g., as shown in FIG. 6) to the distal portion of the scorpion's tail near to the stinger.

When the scorpion is properly restrained by restraints 20 and 30, a small amount of electricity applied by wire 620 will cause the scorpion to express its venom. For example, short pulses of approximately 20 Volts, e.g., a few pulses of three to five seconds duration, will cause the scorpion to express its venom.

Those of ordinary skill will appreciate that the electronics used to control the fan and stimulation of the scorpion's tail via switch 12 are relatively simple. For example, electronic control chip(s) can be housed along with batteries within the chamber coved by plate 440 (shown in FIG. 4D).

Figure 10:
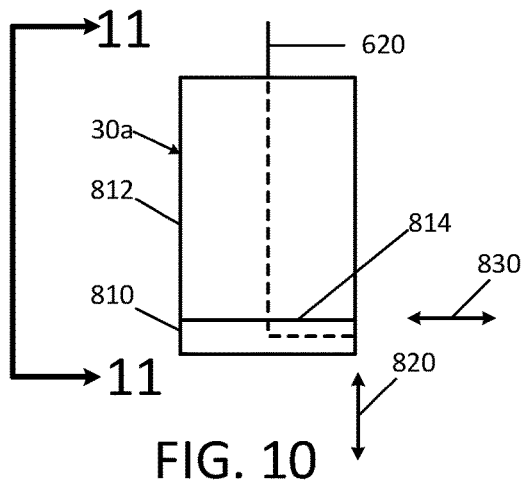
FIG. 10 shows a top view of another embodiment of the tail restraint.

FIG. 10 shows a top view of another embodiment of the tail restraint, here depicted as restraint 30a. As shown, this embodiment of tail restraint 30a includes an arm 810 and a main body 812. Arm 810 is movably coupled to the top surface 101 of unit 10, e.g., so that arm 810 can rotate relative to the top surface 101 about an axis 820. Arm 810 and main body 812 are movably coupled together at coupling 814 (e.g., which can be implemented as one or more hinges), e.g., such that main body 812 can rotate about axis 830 relative to arm 810.

Figure 11A:
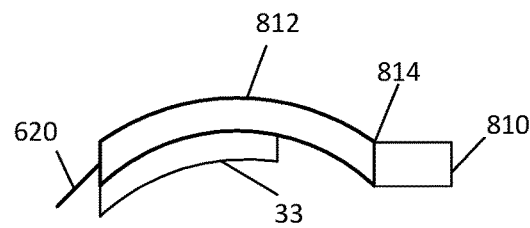
FIG. 11A shows a side view of the tail restraint shown in FIG. 10 from the perspective illustrated by arrow 11-11 in FIG. 10.
Figure 11B:
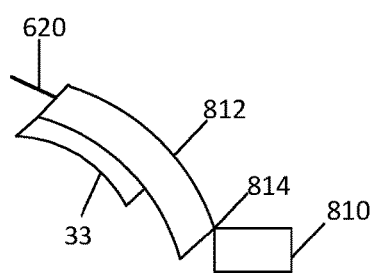
FIG. 11B shows another side view of the tail restraint shown in FIG. 11A with the main section of the restraint in a different position than is shown in FIG. 11A.

FIG. 11A shows a side view of tail restraint 30a taken from the perspective indicated by arrow 11-11 in FIG. 10. FIG. 11B shows another side view of tail restraint 30a again taken from the perspective indicated by arrow 11-11 in FIG. 10. Comparing FIGS. 11A and 11B illustrates how the main body 812 of tail restraint 30a can move relative to the arm 810. As shown in FIG. 11A, the lateral restraints 33 can be longer than as depicted in FIG. 8. Those of ordinary skill will appreciate that the arm 610 and main body 612 of tail restraint 30 (e.g., as depicted in FIG. 6) can also be movably coupled to one another as are arm 810 and main body 812. Similarly, those of ordinary skill will also appreciate that the size of lateral restraints 33 can vary, e.g., being longer as shown in FIG. 11 or shorter as shown in FIG. 8, regardless of which embodiment of the tail restraint is used.

When a tail restraint in which the main body is movable with respect to the arm (e.g., as shown in FIGS. 11A and 11B) is used, the operator would initially place the main body in an open position, e.g., as illustrated in FIG. 11B. The operator would then move arm 810 to a closed position such that it is held to the top surface 101 by clasp 34 (shown in FIG. 2). The operator would then move the main body 812 to a closed position, e.g., as illustrated in FIG. 11A so as to restrict up-down motion of the scorpion's tail. The operator would then move the lateral restraints 33 towards one another so as to restrict side-to-side motion, or wriggling, of the scorpion's tail. The operator would then proceed with cleaning and drying the scorpion's tail and extracting the scorpion's venom as has been described above.

Those of ordinary skill will also appreciate that any single scorpion should have its venom extracted infrequently, e.g., bi-weekly. Further, handling scorpions in the manner described herein is believed to be safe both for the human operator and the scorpion and is further believed to be humane for the scorpion. For example, although unit 10 restrains movements of a scorpion, it does not force the scorpion's body into unnatural, non-anatomic, positions. Rather, the restrained position of a scorpion, as held by restraints 20 and 30, is within the scorpion's natural range of motion.

As shown in FIGS. 3A and 4A, unit 10 has a length L, a width W and a height H. A preferred value for the length L is about seven inches. A preferred value for the width W is about three and a half inches. A preferred value for the height H is about three and a half inches. Those of ordinary skill will appreciate that significant variation of the values for the length L, width W and height H are possible and are embraced within the invention. Further, the dimensions of unit 10 may be adapted depending on the type of scorpion used. The preferred dimensions recited above are believed to be well-adapted for accommodating death stalker scorpions and can be adjusted for use with other types of scorpions. The height H of unit 10 is selected primarily so that the unit fits comfortably within a human hand and so that the operator can manipulate switches 12-15 and restraints 20 and 30 with thumb and fingers while the bottom surface 106 of unit rests in the palm of the hand.

Those of ordinary skill will appreciate that unit 10 can be constructed from inexpensive materials such as plastic or wood. Those of ordinary skill will further appreciate that only modest electrical power is used and unit 10 can be powered, e.g., by conventional triple AAA, double a AA, or other commonly available batteries.

The present embodiments are therefore to be considered in all respects as illustrative and not restrictive, the scope of the invention being indicated by the appended claims rather than by the foregoing description, and all changes which come within the meaning and band of equivalency of the claims are therefore intended to be embraced therein.

What is claimed is:

1. A portable scorpion venom extraction unit, including:
   A. a body restraint having a first end that is movably coupled to a top surface of the unit, the body restraint further having a free-end, the body restraint being movable between an open position and a closed position;
   B. a clasp for holding the free-end when the body restraint is in the closed position;
   C. a first switch for causing the clasp to release the free-end;
   D. a tail restraint movably coupled to the top surface of the unit, the tail restraint being movable between an open position and a closed position, the tail restraint further having first and second lateral restraints;
   E. a venom receptacle holder arm having a first end and a second end, the first end of the holder arm being movably coupled to a back surface of the unit, the holder arm being movable between a stowed position and a deployed position;

F. a venom receptacle attached to the second end of the venom receptacle holder arm;
G. a chamber within the unit for holding a reservoir of cleaning fluid;
H. a second switch configured for expelling a cleaning solution from the reservoir through an irrigation port;
I. an airflow channel;
J. an electric fan mounted within the airflow channel;
K. a third switch for turning the electric fan on and off;
L. an electric wire extending through the tail restraint such that an exposed end of the wire is positioned over the venom receptacle when the holder arm is in the deployed position;
M. a fourth switch for selectively coupling an electric power source to the wire;
   wherein the unit is sized to fit within a hand of a human operator such that a bottom surface of the unit can rest in a palm of the hand, and when the unit is resting in the palm of the operator's hand, each of the first, second, third and fourth switches are reachable by a thumb or fingers of the operator's hand,
   wherein the unit is further sized such that when a scorpion is supported by the top surface of the unit, the body restraint can restrain a body of the scorpion when the body restraint is in the closed position, and such that the tail restraint can restrain the tail of the scorpion when the tail restraint is in the closed position.

2. A unit according to claim 1, the first and second lateral restraints being movably mounted to the tail restraint.

3. A unit according to claim 1, the tail restraint including a tail restraint arm and a tail restraint body.

4. A unit according to claim 3, the tail restraint arm being movably connected to the tail restraint body.

5. A unit according to claim 4, further including a first hinge that connects to the tail restraint arm and the tail restraint body, the first hinge permitting the tail restraint body to rotate with respect to the tail restraint body.

6. A unit according to claim 5, the first and second lateral restraints being movably mounted to the tail restraint body.

7. A unit according to claim 6, the first and second lateral restraints restricting side-to-side motion of a tail of the scorpion when the tail restraint is in the closed position.

* * * * *